United States Patent [19]

Pust

[11] Patent Number: 4,477,403

[45] Date of Patent: Oct. 16, 1984

[54] METHOD OF MAKING AN ELECTROCHEMICAL SENSOR

[75] Inventor: Harold W. Pust, Huntington Beach, Calif.

[73] Assignee: Teledyne Industries, Inc., Los Angeles, Calif.

[21] Appl. No.: 565,538

[22] Filed: Dec. 27, 1983

Related U.S. Application Data

[62] Division of Ser. No. 498,300, May 26, 1983.

[51] Int. Cl.³ ............... C04B 35/14; G01N 27/40
[52] U.S. Cl. .................... 264/104; 264/112; 204/421; 204/424; 204/432; 29/570
[58] Field of Search ............. 429/191, 188, 190, 193, 429/204, 206; 204/410, 414, 421, 424–429, 431, 432; 29/592 R, 570; 264/104, 112, 113, 272.16, 272.12; 252/62.2

[56] References Cited

U.S. PATENT DOCUMENTS

| | | | |
|---|---|---|---|
| 1,389,750 | 9/1921 | Gardiner | 429/190 |
| 1,583,445 | 5/1926 | Collins | 429/190 |
| 1,748,011 | 7/1927 | Dooley | 252/62.2 |
| 1,866,604 | 7/1932 | Siegmund | 252/62.2 |
| 3,172,782 | 3/1965 | Jache | 429/190 X |
| 3,202,611 | 8/1965 | Canty et al. | 252/62.2 |
| 3,271,199 | 9/1966 | Beste et al. | 429/190 |
| 3,305,396 | 2/1967 | Rauter | 429/190 X |
| 3,408,233 | 10/1968 | Parker et al. | 429/204 X |
| 3,556,851 | 1/1971 | Douglas et al. | 429/190 X |
| 3,723,589 | 3/1973 | Kennedy | 264/101 |
| 3,765,942 | 10/1973 | Jache | 429/190 |
| 3,776,779 | 12/1973 | Johnson | 429/190 |
| 4,018,971 | 4/1977 | Sheibley et al. | 429/105 |
| 4,317,872 | 3/1982 | Varma | 429/190 |

Primary Examiner—Howard S. Williams
Assistant Examiner—T. L. Williams
Attorney, Agent, or Firm—Reagin & King

[57] ABSTRACT

A method of making an electrochemical sensor is disclosed in which a liquid electrolyte such as sulfuric acid is blended with fumed silica in an amount sufficient to powderize the mixture. The resultant mixture is compacted under pressure between electrodes to form an electrochemical gas sensor.

6 Claims, 1 Drawing Figure

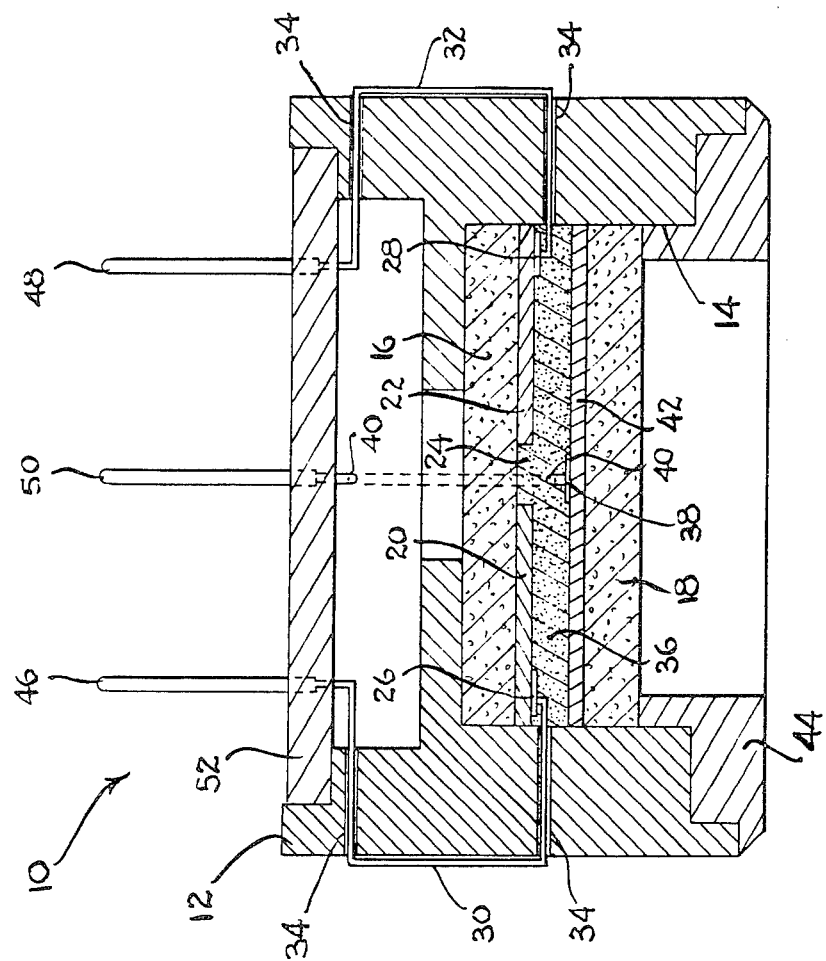

1

METHOD OF MAKING AN ELECTROCHEMICAL SENSOR

BACKGROUND OF THE INVENTION

This invention relates to electrolytes and more particularly, electrolytes for use in electrochemical sensors.

For many years, electrochemical sensors have been used to measure the concentration of certain gases. Typically, such sensors include a cell having two or more electrodes separated by an electrolyte. In the presence of an oxidizable gas, an oxidation-reduction reaction takes place within the cell, creating a sensor output signal in the form of a current flow between the electrodes. The magnitude of the current is a measure of the concentration of the gas.

Many prior art electrochemical sensors employ liquid electrolytes, which are easy to prepare and are highly conductive. However, because these sensors must be designed to prevent leakage of the electrolyte, they are generally larger and heavier than sensors employing non-liquid electrolytes. The liquid electrolyte sensors also tend to be position-sensitive.

Some prior art electrochemical sensors employ solid electrolytes in their construction. These electrolytes are generally prepared from commercially manufactured solid chemicals, and permit the construction of small, lightweight sensors. It has been found, however, that gas sensors using these solid electrolytes generally produce output signals which are not linearly related to measured gas concentration, and which vary significantly as a function of ambient temperature. Accordingly, such sensors are not highly accurate, and require compensation circuitry for their use.

Still other prior art electrochemical sensors employ gelled electrolytes which do not suffer from the position sensitivity of liquid electrolytes. Gelled electrolytes can also be used over a wider range of temperatures and pressures than can liquid electrolytes. However, a major disadvantage of using gelled electrolytes is the tendancy of the liquid in the electrolyte to evaporate, causing the gel to shrink. Such shrinking produces erratic and unreliable sensor performance.

Accordingly, it is an object of the present invention to provide a new and improved electrolyte for use in electrochemical sensors.

It is another object of the present invention to provide a powdered liquid electrolyte for use in electrochemical sensors.

It is yet another object of the present invention to provide an electrochemical sensor using a powdered liquid electrolyte.

SUMMARY OF THE INVENTION

The foregoing and other objects of the invention are accomplished by combining a solution of liquid electrolyte with fumed silica in an amount of silica not less than 25% by weight of the combination to form a powdered liquid. The powdered liquid is placed between porous electrodes in an electrochemical sensor housing and pressure is applied to the electrodes to form a compacted powdered liquid electrolyte between the electrodes.

Other objects, features, and advantages of the invention will become apparent from a reading of the specification when taken in conjunction with the drawing.

BRIEF DESCRIPTION OF THE DRAWING

The sole FIGURE is a cross-sectional view of an electrochemical gas sensor constructed using the powdered liquid electrolyte of the present invention.

DESCRIPTION OF THE PREFERRED EMBODIMENT

According to the present invention, a powdered light is formed by homogenizing a solution of liquid electrolyte with fumed silica in an amount of silica not less than 25% by weight of the combination.

In the prior art, it is well known that silica may be mixed with a liquid electrolyte to form a gelled electrolyte, where the silica acts as a gelling agent. The resultant gelled electrolytes are generally designed for use in batteries. Examples of such electrolytes are disclosed in U.S. Pat. No. 1,389,750, issued Sept. 6, 1921 to W. Gardiner; U.S. Pat. No. 1,583,445 issued May 4, 1926 to N. Collins; U.S. Pat. No. 3,172,782, issued Mar. 9, 1965 to O. Jache; U.S. Pat. No. 3,271,199, issued Sept. 6, 1966 to H. Beste, et al; U.S. Pat. No. 3,305,396, issued Feb. 21, 1967 to R. Router; U.S. Pat. No. 3,556,851 issued Jan. 19, 1971 to D. Douglas, et al; U.S. Pat. No. 3,765,942, issued Oct. 16, 1973 to O. Jache; U.S. Pat. No. 3,776,779, issued Dec. 4, 1973 to B. Johnson; U.S. Pat. No. 4,018,971, issued Apr. 19, 1977 to D. Sheibley, et al; and U.S. Pat. No. 4,317,872, issued Mar. 2, 1982 to B. Varma.

In general, the prior art teaches the use of silica in amounts sufficient to cause the mixture to gel, but teaches away from the use of silica in amounts sufficient to powderize the mixture. One reason powdered electrolytes have not been used successfully is because of their low level of conductivity. Further, even small amounts of evaporation tend to cause major changes in conductivity.

In the present invention, on the other hand, it has been found that powdered liquids may be use successfully in the construction of electrochemical sensors by compacting the powdered liquid under pressure between the sensor electrodes. Such compacting appears to stabilize the conductivity of the electrolyte, and significantly minimizes evaporation.

In a preferred embodiment of the invention, a powdered liquid is formed by combining a 34% solution of reagent grade sulfuric acid with fumed silica in an amount of 50% by weight of the mixture. A typical fumed silica for use in this application is Aerosil 200, supplied by Degussa Corporation, Teterboro, New Jersey. The fumed silica is first placed in a blender, and the corresponding amount of 34% sulfuric acid is slowly added. The mixture is blended at high speed for about five minutes, or until the powdery mix is completely homogeneous. If necessary, the sides of the container should be scraped, and the mixture re-blended to obtain a homogeneous mix. The resultant powdered liquid is pressed between electrodes to form the electrolyte in an electrochemical sensor, as described below.

While the preferred composition of the powdered liquid employs a 34% solution of sulfuric acid, acid solutions having concentrations ranging from 0.1% to more than 40% may also be used. Further, the liquid electrolyte is not limited to sulfuric acid, but can instead be selected from the group of commonly employed liquid electrolytes such as phosphoric acid, acetic acid, potassium hydroxide, hydrochloric acid, nitric acid, potassium chloride, sodium hydroxide and potassium nitrate.

While the preferred amount of fumed silica is approximately 50% by weight of the powdered liquid mixture, amounts ranging from about 25% to about 70% by weight of the mixture may be used. The lower limit on the amount of fumed silica is determined by the minimum amount necessary to fully powderize the liquid. Lesser amounts merely gel the liquid. The upper limit on the amount of fumed silica is determined by the minimum acceptable conductivity of the resultant electrolyte, since greater amounts of silica reduce the conductivity of the mixture. In addition to the Aerosil 200 type fumed silica used in the preferred embodiment, Aerosil 130, Aerosil 150, Aerosil 300, Aerosil 380, Aerosil R972, and Aerosil COK 84 may also be used. It is also envisioned that gelling agents other than fumed silica may be used to produce powdered liquid electrolytes in accordance with the teachings of the invention.

The powdered liquid formed as described above is used to construct an electrochemical gas sensor as follows. Referring to the FIGURE, there is shown a cross sectional view of a carbon-monoxide sensor 10 constructed in accordance with the invention. A housing 12 is provided which is constructed of a relatively inert dielectric material such as high density polyethylene. A generally cylindrical cavity 14 is formed in the housing 12. First and second disk-shaped porous substrates, 16 and 18, respectively, are provided which are each approximately one-hundred and twenty-five thousandths of an inch thick. Each substrate may be formed of porous polyethylene, porous ceramic, glass frit, Teflon membranes or similar materials. The first membrane 16 is placed within the cavity 14 as shown in the FIGURE.

Also provided are reference and auxiliary electrodes 20 and 22, respectively. Each electrode 20 and 22 is in the form of a circular disk which, in the preferred embodiment is constructed of a porous Teflon membrane impregnated with platinum black to form a conductive electrode. The electrodes 20 and 22 are placed in the cavity 14 adjacent the first substrate 16, and are spaced apart, forming a gap 24 between them. Electrical connections are made to the electrodes 20 and 22 using stainless steel washers 26 and 28, respectively, each of which is placed in contact with a respective side of the electrodes 20 and 22. Nickel wires 30 and 32 are welded to the washers 26 and 28, respectively and are routed through openings 34 provided in the wall of the housing 12.

Powdered liquid 36, prepared as described above, is distributed over the electrodes 20 and 22 within the cavity 14. Using a press, the powdered liquid 36 is then compacted against the electrodes 20 and 22 using a pressure of approximately 1000 pounds per square inch. A third stainless steel washer 38 is connected to a wire 40 (also routed through openings, not shown, in the wall of the housing 12) and is placed on the compacted powdered liquid 36.

A disk-shaped working electrode 42 constructed of the same material as the electrodes 20 and 22 is placed in contact with the washer 38. The second porous substrate 18 is then placed adjacent the electrode 42. Using a press, pressure of approximately 2000 pounds per square inch is applied to the second porous substrate to further compact the powdered liquid 36 between the electrodes 20 and 22 and the electrode 42. A retaining ring 44 is affixed in the open end of the cavity 14 to hold the components in place. The wires 30, 32, and 40 are connected to terminal pins 46, 48, and 50 respectively, provided in a header 52. The header 52 is in turn affixed to the end of the housing 12 opposite the ring 44.

The above described sensor 10, having a powdered liquid as an electrolyte, may be used to measure low levels of carbon monoxide. The sensor incorporates a conventional three-electrode system, where a constant potential is maintained between the reference electrode 20 and the working electrode 42. Carbon monoxide is oxidized to carbon dioxide at the working electrode 42, and oxygen is reduced to water at the auxiliary electrode 22.

While the sensor described above employs a three terminal configuration, a conventional two electrode configuration may also be constructed. Further, sensors designed to measure gases other than carbon monoxide, such as hydrogen sulfide, sulfur dioxide, nitrogen oxide and hydrogen, may also be readily constructed using the principles of this invention.

Another advantage of using the powdered liquid electrolyte of the invention in the design of electrochemical sensors is that metals such as nickel, copper and silver may be used to construct the electrodes in place of more costly noble metals such as platinum, gold, and paladium. This is so because the corrosive action of the liquid electrolyte is markedly reduced in the powdered liquid form.

While there have been shown and described preferred embodiments of the invention, it is to be understood that various other adaptations and modifications may be made within the spirit and scope of the invention. It is thus intended that the invention be limited in scope only by the appended claims.

What is claimed is:

1. A method of making an electrochemical sensor, comprising the steps of:
   providing a housing having a cavity;
   providing first and second porous substrates,
   locating the first porous substrate in the cavity;
   providing first and second porous electrodes, each having electrode connection means;
   locating the first porous electrode adjacent the first porous substrate in the cavity;
   providing a powdered liquid formed of a solution of liquid electrolyte blended with fumed silica in an amount of silica not less than 25% by weight of the blend;
   distributing the powdered liquid over the first porous electrode in the cavity;
   compacting the powdered liquid against the first porous electrode by applying pressure to the powdered liquid;
   locating the second porous electrode adjacent the compacted powdered liquid in the cavity;
   locating the second porous substrate adjacent the second porous electrode; and
   applying pressure to the second porous substrate to further compact the powdered liquid between the first and second porous electrodes.

2. The method of claim 1 in which the solution of liquid electrolyte is selected from the group consisting of hydrochloric acid, nitric acid, potassium chloride, phosphoric acid, acetic acid, potassium hydroxide, sodium hydroxide, or potassium nitrate.

3. The method of claim 1 in which the solution of liquid electrolyte is a solution of reagent grade sulfuric acid having a concentration in the range from 0.1% to 40%.

4. The method of claim 1 in which the fumed silica is present in an amount ranging from 25% to 70% by weight of the combination.

5. The method of claim 1 in which the powdered liquid is compacted under pressure ranging from 200 pounds per square inch to 3500 pounds per square inch.

6. A method of making an electrochemical sensor, comprising the steps of:

provdiing a housing having a cavity;

providing first and second porous electrodes, each having electrode connection means;

locating the first porous electrode in the cavity;

providing a powdered liquid formed of a solution of liquid electrolyte blended with fumed silica in an amount of silica not less than 25% by weight of the blend;

distributing the powdered liquid over the first porous electrode in the cavity;

compacting the powdered liquid against the first porous electrode by applying pressure to the powdered liquid;

locating the second porous electrode adjacent the compacted powdered liquid in the cavity; and applying pressure to the second porous electrode to further compact the powdered liquid between the first and second porous electrodes.

* * * * *